United States Patent
McCombe et al.

(10) Patent No.: US 7,951,203 B2
(45) Date of Patent: *May 31, 2011

(54) INTERBODY FUSION DEVICE

(75) Inventors: Peter McCombe, Brisbane (AU); B. Thomas Barker, Bartlett, TN (US); William Sears, St. Leonards (AU); David Warmbold, Collierville, TN (US); Russell Powers, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 639 days.

This patent is subject to a terminal disclaimer.

(21) Appl. No.: 12/021,107

(22) Filed: Jan. 28, 2008

(65) Prior Publication Data

US 2008/0119937 A1    May 22, 2008

Related U.S. Application Data

(63) Continuation of application No. 10/404,262, filed on Apr. 1, 2003, now Pat. No. 7,326,251.

(51) Int. Cl.
*A61F 2/44* (2006.01)
(52) U.S. Cl. .................................... 623/17.16
(58) Field of Classification Search .............. 623/1.3, 623/1.31, 16.11, 17.11–17.16, 21.18, 23.48
See application file for complete search history.

(56) References Cited

U.S. PATENT DOCUMENTS

| | | | |
|---|---|---|---|
| 5,306,308 A * | 4/1994 | Gross et al. | 623/17.16 |
| 5,425,772 A | 6/1995 | Brantigan | |
| 5,443,514 A | 8/1995 | Steffee | |
| 5,658,337 A | 8/1997 | Kohrs et al. | |
| 5,888,224 A * | 3/1999 | Beckers et al. | 623/17.16 |
| 5,888,226 A * | 3/1999 | Rogozinski | 623/17.16 |
| 5,904,719 A * | 5/1999 | Errico et al. | 623/17.16 |
| 6,174,311 B1* | 1/2001 | Branch et al. | 606/86 A |
| 6,436,139 B1* | 8/2002 | Shapiro et al. | 623/17.11 |
| 6,726,722 B2* | 4/2004 | Walkenhorst et al. | 623/17.16 |
| 7,326,251 B2* | 2/2008 | McCombe et al. | 623/17.16 |
| 7,621,958 B2* | 11/2009 | Zdeblick et al. | 623/17.16 |
| 7,637,951 B2* | 12/2009 | Michelson | 623/17.11 |
| 2002/0026242 A1* | 2/2002 | Boyle et al. | 623/17.11 |
| 2004/0102847 A1 | 5/2004 | Sato et al. | |
| 2004/0127922 A1* | 7/2004 | Cull et al. | 606/166 |
| 2004/0148026 A1* | 7/2004 | Bonutti | 623/16.11 |

OTHER PUBLICATIONS

PLIF Spacer Instruments Technique Guide, SYNTHES Spine.
Jaslow, Irwin A., M.D., "Intercorporal Bone Graft in Spinal Fusion After Disc Removal" National Library of Medicine, Dec. 2000, pp. 215-218.
Brantigan, John W.M M.D., "Lumbar I/F Cage Implants and Instruments", DePuy AcroMed Product Catalog, Sep. 1999, pp. 1-12.
Lowe, Thomas G., "CD Horizon Multi Axial Screw", Medtronic Sofamor Danek Brochure, Rev. A, Nov. 2002, pp. 1-20.
Burkus, J. Kenneth, M.D., "TSRH-3D Spinal Instrumentation Surgical Technique", Medtronic Sofamor Danek Brochure, Rev. B, May 2003, pp. 1-31.

* cited by examiner

*Primary Examiner* — Corrine McDermott
*Assistant Examiner* — Cheryl Miller (57) ABSTRACT

An interbody spacer includes concave lateral surfaces extending at an angle with respect to the longitudinal axis. In one aspect, the interbody spacer includes upper and lower convex surfaces defined by an arc extending from a center point offset from the spacer midpoint. In another aspect, lateral edges of the upper and lower surfaces are also defined by convex arcs extending from a center point offset from the spacer midpoint.

13 Claims, 7 Drawing Sheets

INTERBODY FUSION DEVICE

CROSS-REFERENCE TO RELATED APPLICATION

The present disclosure is a continuation of and claims priority to U.S. Ser. No. 10/404,262, filed Apr. 1, 2003, and entitled, "Interbody Fusion Device," now U.S. Pat. No. 7,326,251, hereby incorporated by reference in its entirety.

BACKGROUND INFORMATION

The present invention relates to devices adapted for spacing between two adjacent vertebrae.

It is known that if an intervertebral disc is damaged, it can be removed and the resulting space between the two adjacent vertebrae may be filled with a bone growth inducing substance to promote a boney fusion across the disc space. Fixation devices external to the disc space have been utilized to maintain the position of the adjacent vertebrae while the intervening material fuses with adjacent bone to form a boney bridge. As an alternative or in conjunction with fixation devices, load bearing spacers, such as artificial devices or bone grafts, may be placed in the empty disc space. These spacers transmit the loading from one adjacent vertebra to the other adjacent vertebra during the healing process. Such spacers may be provided in a variety of forms.

A need exists for improvements to existing interbody spacers and the present invention is directed to such need.

SUMMARY OF THE INVENTION

The present invention provides an improved interbody fusion device adapted for spacing two adjacent vertebral bodies. In one preferred aspect but without limitation to embodiments incorporating alternative features, the spacer includes lateral surfaces that extend at an angle with respect to the longitudinal axis. In another preferred aspect, the spacer includes upper and lower convex surfaces adapted for engagement with adjacent vertebrae. Preferably, the convex surfaces are defined by an arc with a center point offset from the device midpoint, thereby establishing a spacer that may induce angulation when positioned in the disc space between adjacent vertebrae. In still a further preferred aspect, the lateral edges of the upper and lower surfaces are convex. Still more preferably, the center point for the arc defining the lateral edges is offset from the midpoint of the device.

The present invention also provides an inserter for use in combination with an interbody spacer. In a preferred embodiment, the inserter has a gripping end with a length approximately the length of the implant and, a width and height equal to or less than the width and height of the implant.

The present invention also provides a method for manufacturing an improved interbody spacer. In one preferred aspect of the method, one or more radiopaque markers is positioned in the spacer material and is shaped to conform to the exterior geometry of the implant.

These and other aspects and advantages of the present invention will become apparent to those skilled in the art from the description of the preferred embodiments set forth below.

DETAILED DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

Figure 1:
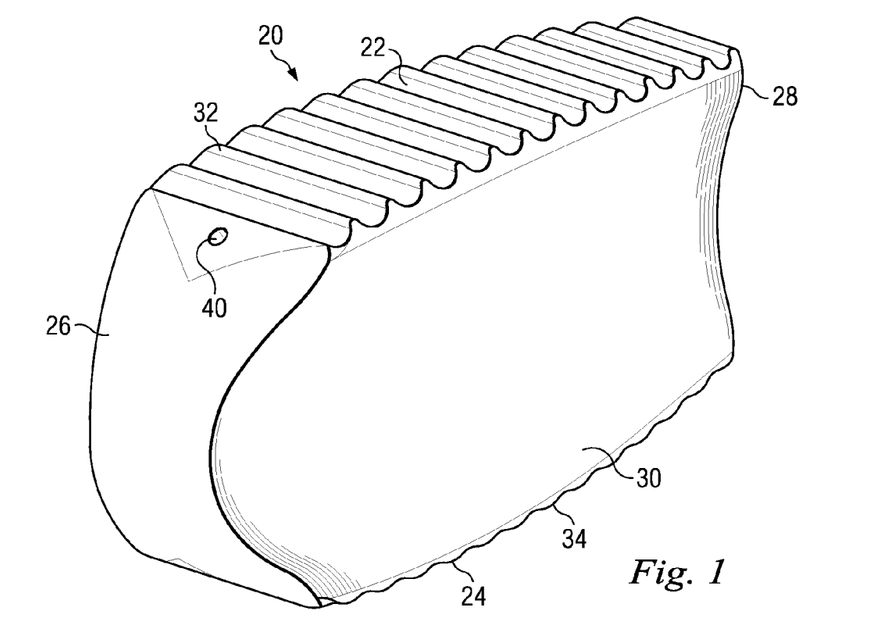
FIG. 1 is a perspective view of an implant according to the present invention.
Figure 2:
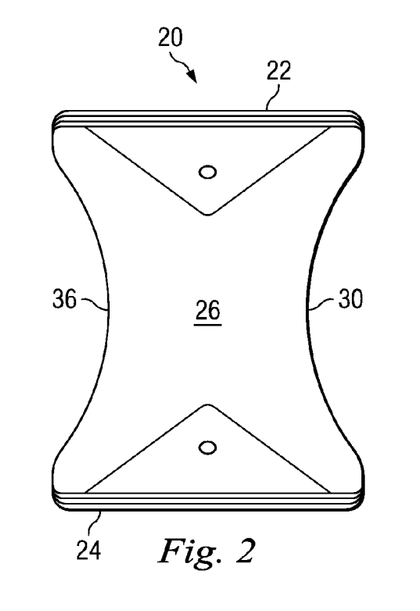
FIG. 2 is an front end view of the implant of FIG. 1.

Referring now to FIGS. 1 and 2, there is shown an interbody spacer 20 configured for placement between two adjacent vertebral bodies. Spacer 20 includes a top surface 22 and a bottom surface 24 spaced from one another by lateral surface 30 and lateral surface 36. Top surface 22 and bottom surface 24 terminate in rear end 28 and front portion 26. Top surface 22 includes a series of projections 32 and bottom surface 24 includes a similar series of projections 34. In a preferred aspect, implant 20 is formed of a radiolucent material and a radiopaque marker 40 is embedded within the material. Implant materials may include PEEK, other polymers, composites, biocompatible metals such as stainless steel, titanium, tantalum, bone, ceramic, or resorbable polymers. Materials are listed by way of example and without limitations as to the material that may form the implant according to the present invention. Furthermore, the implant 20 is illustrated as a solid body of substantially uniform material. It will be appreciated that teachings of the present invention may be applied to interbody fusion devices having internal chambers or pores for receiving bone growth promoting material. Still further, the implant may be formed of layers of non-uniform material, such as bone and other composited materials, to define an external geometry incorporating the teachings of the present invention.

Figure 3A:
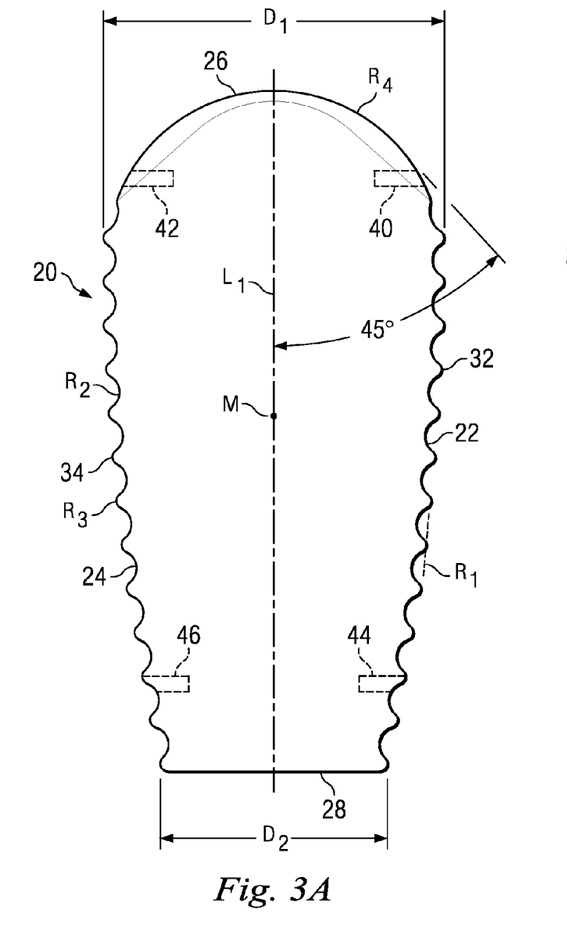
FIG. 3A is a side elevation view of the implant of FIG. 1.
Figure 3B:
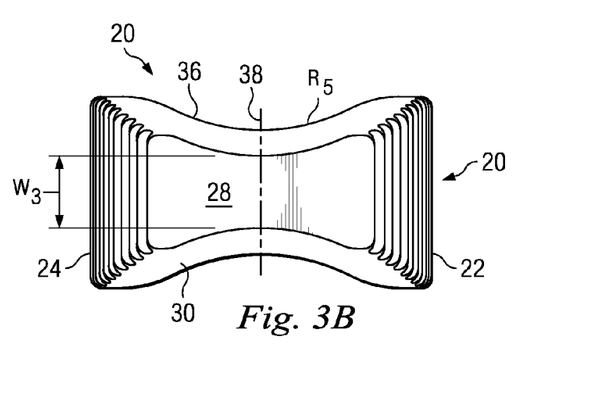
FIG. 3B is a rear end view of the implant of FIG. 3A.
Figure 3C:
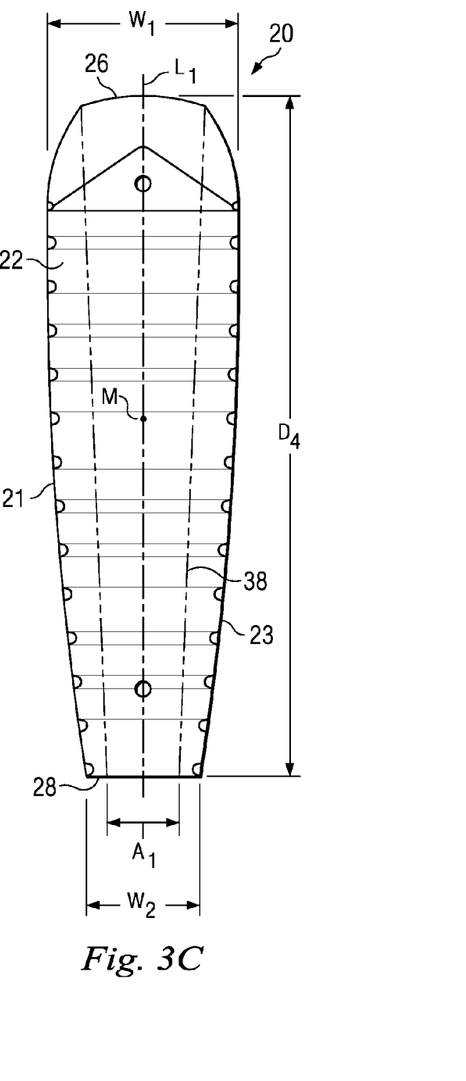
FIG. 3C is a top view of the implant of FIG. 3A.
Figure 5:
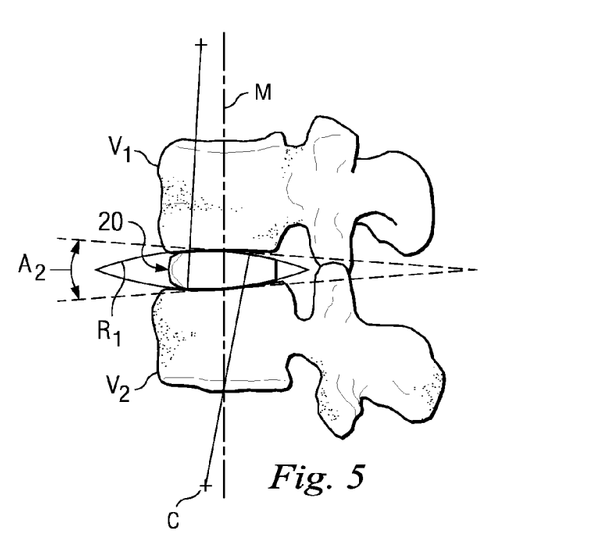
FIG. 5 is a stylized side view of two adjacent vertebrae with an implant according to the present invention disposed in the disc space.

Referring now to FIGS. 3A through 3C, there are shown various views of implant 20 in accordance with one aspect of the present invention. Top surface 22 has a convex shape with a radius of curvature R1 extending from front portion 26 to rear end 28. In a similar manner, bottom surface 24 has a convex shape with a radius of curvature from front portion 26 to rear end 28 substantially identical to R1. The height of the device at the front end 26 is D1. The height of implant 20 at the rear end 28 is D2. As illustrated in FIG. 3A, D1 is substantially greater than D2. The relationship between D1 and D2 is created by the location of center point C for the radius of curvature R1 for top surface 22 and the corresponding location of the center point for the radius when forming bottom surface 24 (FIG. 5). More specifically, the center point C for R1 is located more anteriorly towards the front portion 26. Thus, the center point C for R1 is longitudinal offset from midpoint M of the device which is equidistant from front end 26 and rear end 28. In the specific embodiment illustrated in FIG. 3A, D1 is approximately 13.6 millimeters and D2 is approximately 9 millimeters. The arc center point C of R1 is located approximately 18.4 millimeters along the longitudinal axis L1 from the posterior end 28 toward anterior end 26 and R1 has a length of approximately 75 millimeters. The center point is located approximately 68.2 millimeters from longitudinal axis L1 extending away from surface 22 for the formation of that surface. In a mirror image about the longitudinal axis, the arc center point for the formation of surface 24 is approximately 68.2 millimeters from L1 extending away from surface 24 and 18.4 millimeters from posterior end 28 along the longitudinal axis.

Referring now to FIGS. 3C and 5, implant 20 has a length D4 from front end 26 to rear end 28. In the illustrated embodiment of the present invention, D4 is approximately 27 millimeters making the device suitable for some applications in the lumbar spine. Thus, with the arc center point for R1 positioned at substantially 18.4 millimeters from posterior end 28, the arc of rotation for R1 is approximately 5 millimeters more anteriorly towards front end 26 resulting in the shape of the implant shown in side view FIG. 3A. The resulting angulation established between D1 and D2 is approximately twelve degrees (12°). FIG. 5 illustrates implant 20 disposed between two vertebrae V1 and V2. Implant 20 establishes an angulation A2 of approximately 12 degrees (12°) between vertebrae V1 and V2.

Each of the top surface 22 and the bottom surface 24 include a series of projections 32 and 34, respectively. Each projection is rounded to eliminate an abrupt surface feature that may have a tendency to engage or tear soft tissue during insertion. In a preferred aspect, each projection peak has a convex radius R3 and a trough radius R2 extending between projections. In a preferred aspect, R3 is approximately 0.25 millimeters and R2 is approximately 0.8 millimeters.

Implant 20 is provided with a series of radiopaque markers to accommodate visualization of the implant during and after insertion into an intervertebral disc space when the implant is formed of substantially radiolucent material. Radiopaque markers 40 and 42 are positioned at the front or anterior portion of the device at the transition point between front portion 26 and top surface 22 and bottom surface 24, respectively. Radiopaque markers 44 and 46 are positioned on the top surface 22 and the bottom surface 24, respectively, adjacent posterior end 28. In a preferred aspect, radiopaque markers 40, 42, 44 and 46 are pins inserted into the implant material prior to formation of the exterior geometry. As illustrated in FIG. 3A, each of the radiopaque markers has an exterior surface substantially identical to and co-terminus with the geometry of the adjacent exterior surface of the implant. Thus, it would be appreciated that upon implantation, a surgeon may be able to correctly visualize through x-ray imaging or other techniques the exact relationship between the surface of the implant and the surrounding bone structures.

Referring now to FIG. 3B, there is shown an end view from posterior end 28 of implant 20. Lateral surfaces 30 and 36 are substantially concave and extend from top surface 22 to bottom surface 24. The radius of curvature for the concave surfaces is illustrated as R5. In the preferred embodiment illustrated in FIG. 3B, R5 is approximately 7.5 millimeters. Posterior end 28 has a width W3 at its midline 38. With reference to FIGS. 3B and 3C, lateral concave surfaces 30 and 36 are formed at an angle A1 with respect to longitudinal axis L1. In a preferred aspect, angle A1 is approximately four and one-quarter degrees (4.25°). As illustrated in FIG. 3C, the width of the material forming the implant at midline 38 increases linearly from width W3 at posterior end 28 to a substantially greater width at anterior end 26. Thus, lateral surfaces 30 and 36 have a concave shape extending from top surface 22 to bottom surface 24 and project at an angle A1 with respect to each other as they extend from posterior end 28 to anterior end 26. This geometrical configuration provides the central portion of the implant with a tapering geometry of increasing thickness extending from posterior end 28 to anterior end 26.

FIG. 3C illustrates a top view of implant 20 in accordance with another aspect of the present invention. The convex lateral edges 21 and 23 of top surface 22 are defined by radius R6 in a mirror image fashion about the longitudinal axis L1. The arc center point of radius R6 defining lateral edge 21 is not aligned with midpoint M of implant 20. In a preferred aspect of the present invention, arc center of radius R6 is located towards the anterior end 26 of the device and has a radius length of approximately 150 millimeters. In a preferred aspect, the arc center point of R6 is located 21.7 millimeters from posterior end 28 along the longitudinal axis L1 and 146.2 millimeters from longitudinal axis L1. The convex lateral edges 21 and 23 of top surface 22 defined by a center point offset from the device midpoint M define a device that increases from width W1 at posterior end 28 to width W2 at anterior end 26 in a non-linear fashion. In a preferred aspect of the illustrated embodiment, W1 is approximately 4.5 millimeters and W2 is approximately 7.5 millimeters. The formation and shape of the convex lateral edges of bottom surface 24 are substantially identical to the convex lateral edges 21 and 23. In another preferred aspect, anterior end 26 has a rounded insertion end set at an angle of approximately forty-five degrees (45°) from longitudinal axis L1 between top surface 22 and bottom surface 24. Additionally, the insertion end is rounded with a radius R4. In a preferred aspect, radius R4 is approximately 6.8 millimeters.

Figure 4A:
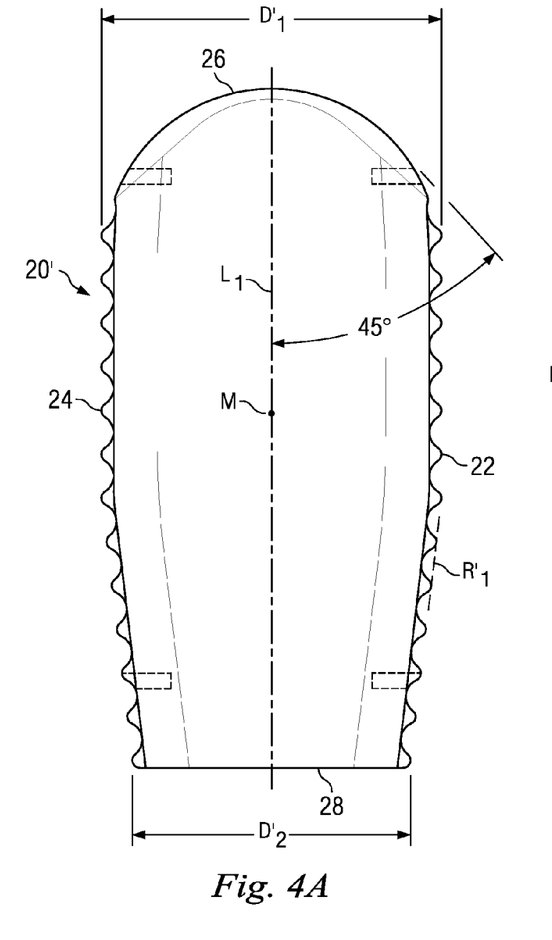
FIG. 4A is a side elevational view of an alternative embodiment according to another aspect of the present invention.
Figure 4B:
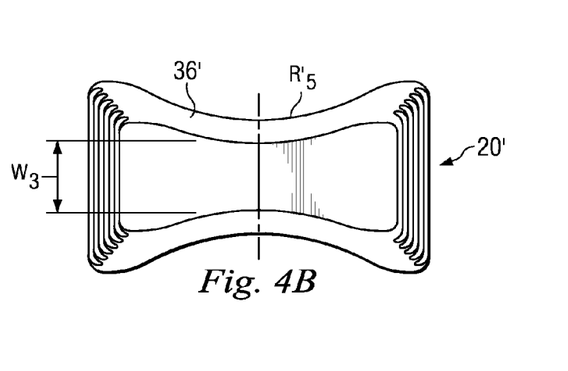
FIG. 4B is an end view of the implant of FIG. 4A.
Figure 4C:
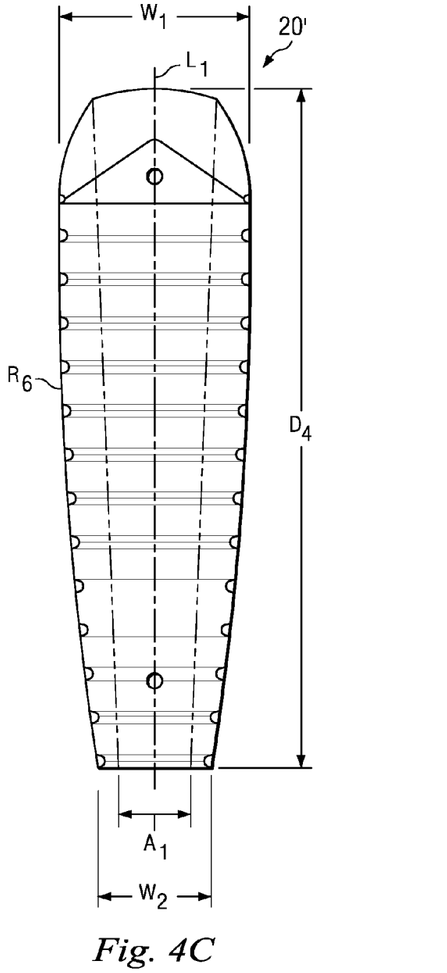
FIG. 4C is a top view of the implant of FIG. 4A.
Figure 6:
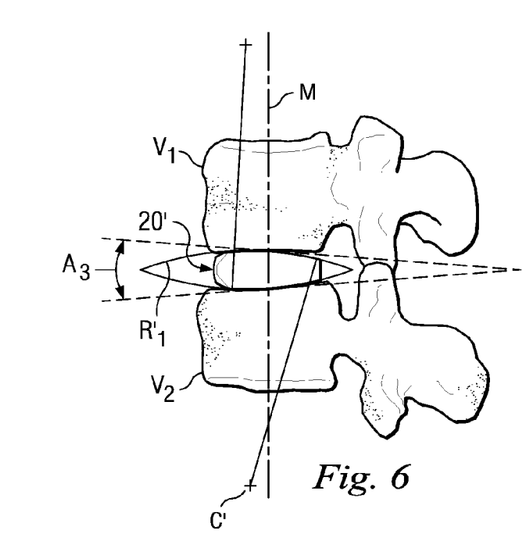
FIG. 6 is a stylized side view of two adjacent vertebrae with an alternative implant according to the present invention disposed in the disc space.
Figure 7:
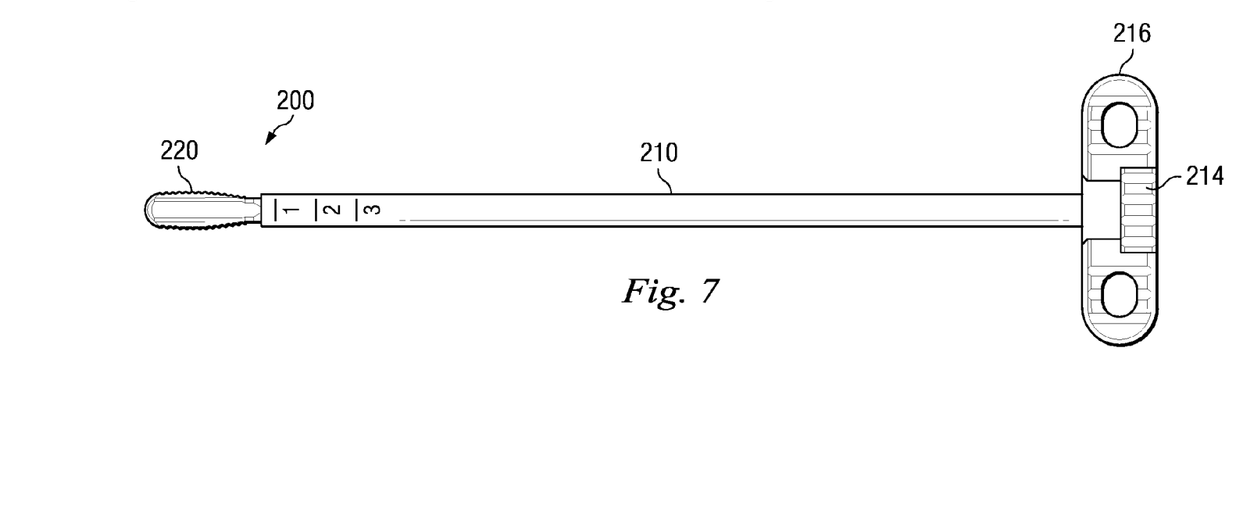
FIG. 7 is a side view of an implant and an inserter in accordance with another aspect of the present invention.
Figure 8:
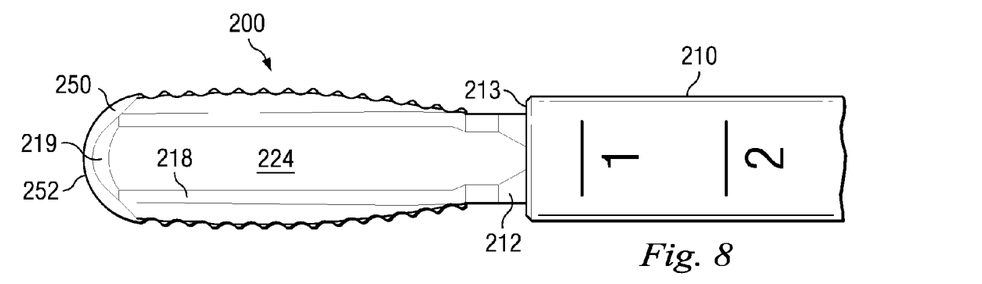
FIG. 8 is an enlarged view of a portion of FIG. 7.

Referring now to FIGS. 4A through 4C, there is shown an alternative embodiment in accordance with another aspect of the present invention. Spacing implant 20' is shown with features similar to implant 20 of FIGS. 3A through 3C. Unless otherwise noted, the features of implant 20' are substantially identical to the features of implant 20. Implant 20' has a radius R1' of approximately 75 millimeters. The center point C' of radius R1' differs from the center point C of radius R1 (see FIGS. 5 and 6). While still located towards the anterior portion of the device, arc center point C' is located closer to the midpoint M of implant 20'. In a preferred aspect, the arc center point C' of R1' is located approximately 14.9 millimeters from posterior end 28 along longitudinal axis L1 and approximately 68 millimeters from longitudinal axis L1. As illustrated in FIG. 6, the resulting height changes are that D1' is approximately 14 millimeters and D2' is approximately 11 millimeters. The resulting change in the center point for the radius R1' creates an implant that provides six degrees (6°) angulation between top surface 22 and bottom surface 24 as the device extends from anterior end 26 to posterior end 28.

Thus, vertebrae V1 and V2 are space by implant 20' at an angle A3. In a preferred aspect, angle A3 is approximately six degrees (6°). Additionally, the radius of curvature of concave lateral surfaces 36' is modified with a radius of curvature of R5'. In the illustrated embodiment, R5' is approximately 5.2 millimeters with a center point extending with a substantial alignment with a longitudinal axis L1 of the device. As with the previously described embodiment, concave lateral surfaces extend to an angle A1 with respect to each other.

The above described implant has included a variety of improved features. While all of these features have been disclosed with reference to the described embodiment, it will be appreciated that one or any combination of features may be utilized with an improved interbody spacer. Further, while specific dimensions were disclosed suitable for spinal anatomy in the lumbar spine of some patients, a spacer may be configured with other dimensions suitable for interbody spacers at various levels, lumbar, thoracic, and cervical, of the spine for a variety of patient populations. For example, in an average patient population the anterior height of the device may range from 4 millimeters to 18 millimeters. Similarly, the posterior height of the device may range from 2 millimeters to 16 millimeters. Within this range, the longitudinal offset of the center point defining the arc of the top and bottom surfaces may be adjusted to create lordotic angulations ranging from 0 to 20°. Further, while a radius of approximately 75 millimeters has been shown for the purpose of illustrating the convex arc of the top and bottom surfaces, alternative radii lengths ranging from 120 millimeters to 30 millimeters may be used. It is anticipated that such radii may approximate a wide range of spinal anatomies. A radius of approximately 60 millimeters may be useful for implantation in smaller disc spaces.

Figure 9:
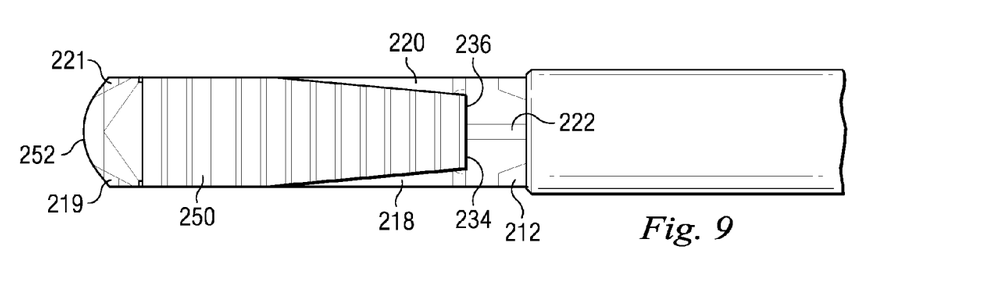
FIG. 9 is a top view of the implant and inserter of FIG. 8.
Figure 10:
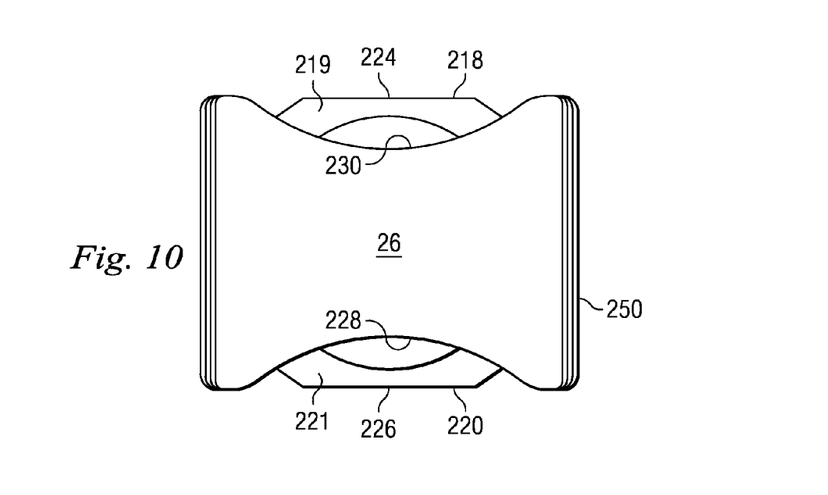
FIG. 10 is an enlarged end view of the implant and inserter of FIG. 9.

Referring now to FIGS. 7 through 10, there is shown a combination 200 of an implant 220 engaged with an insertion tool 210. Insertion tool 210 includes an inner shaft 212 slidably disposed within an outer tube 213. Inner shaft 212 includes a pair of opposing branches 218 and 220 spaced apart by gap 222. It will be appreciated that thumb wheel 214 may be rotated with respect to outer tube 213 to draw inner shaft 212 proximally thereby urging opposing branches 218 and 220 toward each other. Branch 218 has a substantially flat outer surface 224 that extends along much of the length of implant 250. Branch 218 terminates in a tapered tip 219. Branch 220 has a substantially flat outer surface 226 and terminates in a tapered tip 221. As shown in FIG. 9, tapered tips 219 and 221 are in substantial conformance with blunt nose 252 of implant 250 to form a substantially continuous smooth insertion end. Gripping branches 218 and 220 are substantially coterminous with the front end of implant 250. The gripping branches extend along lateral surfaces of the implant from the posterior end to immediately adjacent the anterior end 252 of the implant. Referring to FIG. 10, gripping branch 218 has an inner gripping surface 230 having a convex surface substantially mating with the concave lateral surface of the implant. In a similar manner, gripping branch 220 has a gripping surface 228 having a convex surface substantially mating with the concave lateral surface of the implant. As a result, rotational force applied to the implant by the gripping branches is distributed along the entire length of the implant. Further, the mating of the concave and convex surfaces of the implant and driver inhibits the concentration of force at a particular location during rotation. As a result, less implant material is needed, or may be a weaker material such as bone, to counteract the rotational forces that may be experienced during rotation within the disc space. Additionally, each gripping branch 218 and 220 includes a shoulder 234 and 236, respectively, adapted to abut the posterior end of the implant to transmit impaction force during insertion.

Referring to FIG. 9, the maximum width of the gripping branches is substantially equal to or less than the maximum width of the implant 250. Thus, the surgical access necessary to implant the spacer 250 is solely a function of the size of the implant since the inserter is no larger in width or height than the implant itself.

Figure 11:
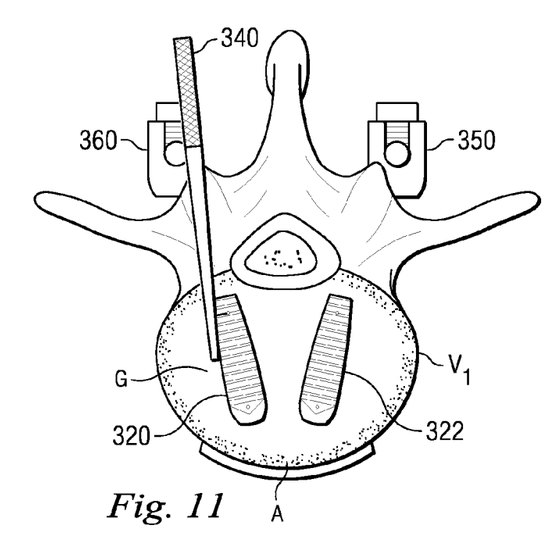
FIG. 11 is a top view of a pair of implants according to the present invention associated with an intervertebral disc space.
Figure 12:
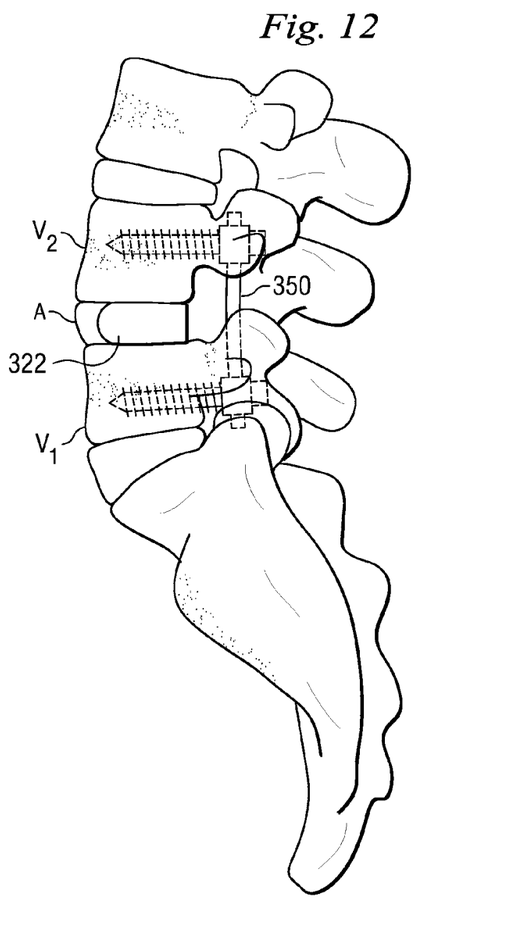
FIG. 12 is a lateral view of an implant disposed in the disc space between two adjacent vertebrae.
Figure 13:
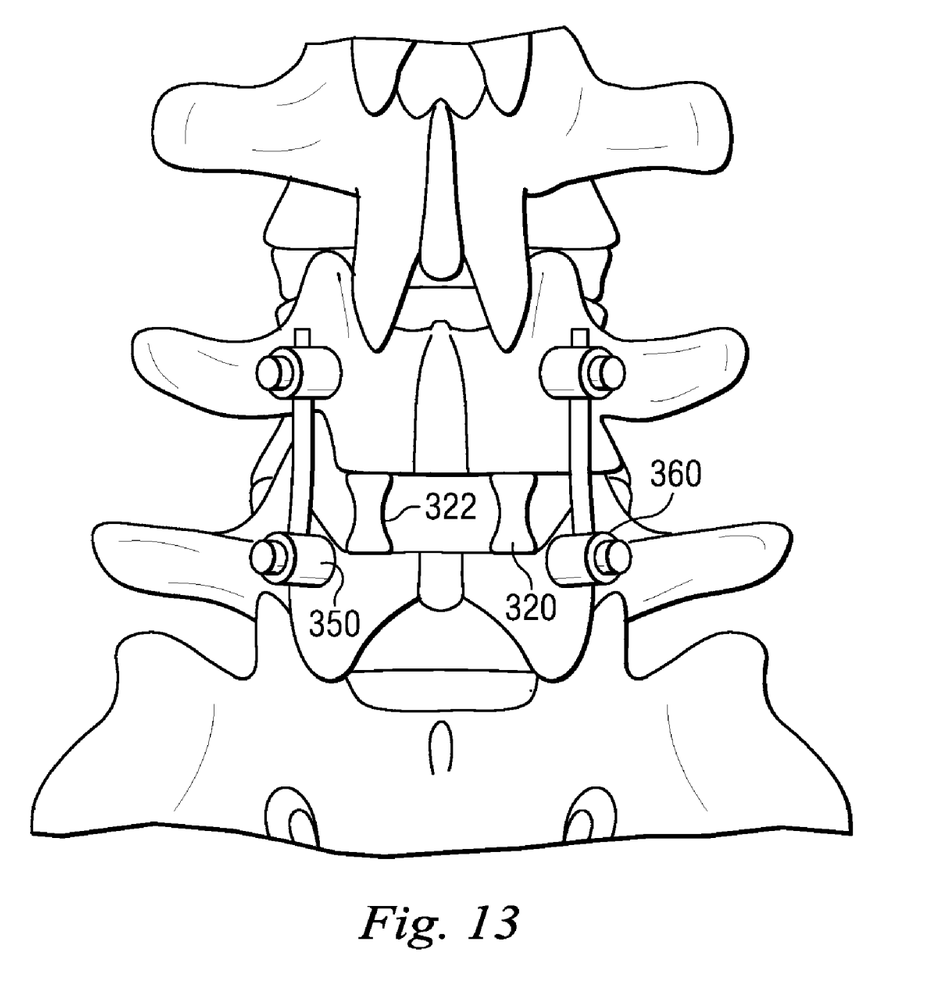
FIG. 13 is a posterior view of a pair of implants disposed in the disc space between two adjacent vertebrae.

FIGS. 11 through 13 illustrate a pair of implants 320 and 322 formed according to the present invention surgically implanted in a disc space between two adjacent vertebrae V1 and V2. Implants 320 and 322 may be impacted directly into the disc space with the upper and lower bone engaging surfaces positioned for immediate engagement with vertebrae V1 and V2. Alternatively, one or both implants may be inserted into the disc space with the bone engaging surfaces positioned laterally and rotated into the spacing position after insertion into the disc space. It will be appreciated that the smooth, rounded features of the implants according to the present invention may limit the potential to snag or abrade soft tissue, including neurological structures, during the insertion procedure. Still further, the bullet nose blunt shape of the anterior end of the implant prevents damage to the anterior annulus A in the event that the implant is advanced too far anteriorly during implantation.

As shown best in FIGS. 11 and 13, graft material G may positioned around the lateral aspects of each implant 320 and 322 to completely fill the disc space annulus with graft material between and outside the spacers. The concave lateral surfaces of each implant maximize the amount of graft material G that may be place in the disc space. Additionally, while the narrow central portion of the implant maximizes graft material, the upper and lower bone engaging surfaces provide substantially greater surface area for engaging the endplates of vertebrae V1 and V2. A tool 340 may be used to advance bone graft into the disc space. Tool 340 may be guided off the concave lateral surfaces of the implants. An additional feature of a spacer embodiment disclosed herein is that the rear end 28 has a width transverse to the longitudinal axis that is smaller than the width adjacent the front portion 26. Thus, more graft material may be inserted adjacent the posterior portion of the implants. Additionally, the tapering lateral surfaces of the implant tend to act like a funnel or ramp as compressive force is applied from the posterior direction to intervening graft material thereby urging graft material into compressive engagement with the vertebral endplates. Fixation implants 350 and 360 may be provided outside the disc space to provide further stabilization. If slight adjustments to the angle of lordosis between vertebrae V1 and V2 is desired, a distraction or compression tool may be applied to implants 350 and 360 move the vertebrae across the convex upper or lower surface of the implants 320 and 322 to modify the angulation between V1 and V2.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. One of ordinary skill will be able to effect various alterations, substitutions of equivalents and other changes without departing from the broad concepts imparted herein. It is, therefore, intended that the letters patent issued hereon be limited only by the definition contained in the appended claims and equivalents thereof.

We claim:

1. A spacer for positioning between two adjacent vertebrae, comprising:
   a convex front surface;
   a substantially planar rear surface positioned opposite the front surface;
   a top surface extending between the front and rear surfaces;
   a bottom surface opposite the top surface, the bottom surface extending between the front and rear surfaces;
   a first concave side surface extending between the front and rear surfaces and extending between the top and bottom surfaces; and
   a second concave side surface opposite the first side surface, the second side surface extending between the front and rear surfaces and extending between the top and bottom surfaces;
   wherein the first and second concave side surfaces extend at an oblique angle with respect to one another;
   wherein the spacer has a height between the top surface and the bottom surface that is greater than a maximum width between the first side surface and the second side surface.

2. The spacer of claim 1, wherein the front surface has an arc of convexity extending between the top surface and the bottom surface.

3. The spacer of claim 2, wherein the front surface has an arc of convexity extending between the first side surface and the second side surface.

4. A spacer for positioning between two adjacent vertebrae, comprising:
   a convex front surface;
   a substantially planar rear surface positioned opposite the front surface;
   a top surface extending between the front and rear surfaces;
   a bottom surface opposite the top surface, the bottom surface extending between the front and rear surfaces;
   a first concave side surface extending between the front and rear surfaces and extending between the top and bottom surfaces; and
   a second concave side surface opposite the first side surface, the second side surface extending between the front and rear surfaces and extending between the top and bottom surfaces;
   wherein the first and second concave side surfaces extend at an oblique angle with respect to one another;
   wherein the spacer has a height between the top surface and the bottom surface that is greater than a maximum width between the first side surface and the second side surface; and
   wherein the first side surface has an arc of concavity extending between the top surface and the bottom surface.

5. The spacer of claim 4, wherein the second side surface has an arc of concavity extending between the top surface and the bottom surface.

6. The spacer of claim 5, wherein the oblique angle is substantially constant along the length of the first and second side surfaces.

7. A spacer for positioning between adjacent vertebrae, comprising:
   an elongated central body portion having a front end, a rear end and a central longitudinal axis extending between the front end and the rear end;
   a top surface extending along the longitudinal axis between the front end and the rear end, the top surface for placement against an upper vertebra;
   an opposing bottom surface extending along the longitudinal axis between the front end and the rear end, the bottom surface configured for placement against a lower vertebra,
   a first lateral surface positioned between the top surface and the bottom surface, a first majority of the first lateral surface being concave with a vertical arc of concavity extending substantially from the top surface to the bottom surface; and
   an opposite second lateral surface positioned between the top surface and the bottom surface, a second majority of the second lateral surface being concave with a vertical arc of concavity extending substantially from the top surface to the bottom surface;
   wherein the first majority of the first lateral surface and the second majority of the second lateral surface each extend longitudinally at a non-parallel angle with respect to the longitudinal axis;
   wherein a height extending between the top and bottom surfaces is greater than a width extending between the first and second lateral surfaces at each point along the longitudinal axis.

8. The spacer of claim 7, wherein the first lateral surface and the second lateral surface extend at an angle greater than 3 degrees with respect to each other.

9. The spacer of claim 8, wherein the front end has a first width between the first and second lateral surfaces substantially transverse to the longitudinal axis, and the rear end has a second width between the first and second lateral surfaces substantially transverse to the longitudinal axis, the first width greater than the second width.

10. The spacer of claim 7, wherein the top surface and the bottom surface each include a series of projections extending substantially transverse to the longitudinal axis.

11. The spacer of claim 10, wherein the projections each have a peak with a radius greater than 0.2 millimeters.

12. The spacer of claim 7, wherein a majority of the body portion comprises a radiolucent material.

13. The spacer of claim 12, further comprising at least one radiopaque marker positioned within the body portion such that an exterior surface of the radiopaque marker is coplanar with at least a portion of the top or bottom surfaces.

* * * * *